(12) United States Patent
Shitoto

(10) Patent No.: US 6,716,213 B2
(45) Date of Patent: Apr. 6, 2004

(54) SPINAL-ROD CONNECTING APPARATUS AND A CONNECTOR THEREOF

(76) Inventor: Hideo Shitoto, 1-27-3-1102 Nishigahara, Kita-ku, Tokyo (JP), 114-0024

( * ) Notice: Subject to any disclaimer, the term of this patent is extended or adjusted under 35 U.S.C. 154(b) by 18 days.

(21) Appl. No.: 09/983,525

(22) Filed: Oct. 24, 2001

(65) Prior Publication Data

US 2003/0078580 A1 Apr. 24, 2003

(51) Int. Cl.[7] ............................................... A61B 17/70
(52) U.S. Cl. ......................................... 606/61; 606/72
(58) Field of Search ............................. 606/60, 61, 72, 606/73

(56) References Cited

U.S. PATENT DOCUMENTS

| | | | | |
|---|---|---|---|---|
| 2,439,995 A | * | 4/1948 | Thrailkill | |
| 5,129,900 A | * | 7/1992 | Asher et al. | 606/61 |
| 5,254,118 A | * | 10/1993 | Mirkovic | 606/61 |
| 5,306,275 A | * | 4/1994 | Bryan | 606/61 |
| 5,474,551 A | * | 12/1995 | Finn et al. | 606/61 |
| 5,498,262 A | * | 3/1996 | Bryan | 606/61 |
| 5,643,259 A | * | 7/1997 | Sasso et al. | 606/61 |
| 5,643,260 A | * | 7/1997 | Doherty | 606/61 |
| 5,669,910 A | * | 9/1997 | Korhonen et al. | 606/61 |
| 5,947,965 A | * | 9/1999 | Bryan | 606/61 |
| 6,015,409 A | * | 1/2000 | Jackson | 606/61 |

* cited by examiner

*Primary Examiner*—Ralph A. Lewis
(74) *Attorney, Agent, or Firm*—Jacobson Holman PLLC

(57) ABSTRACT

To avoid requiring physicians to machine a connecting apparatus in the operating room, and to easily and accurately attach and secure rods and bone screws through the appropriate combination of connectors; a feature made possible by multiple connectors, each of which includes a through-hole through which a rod can be inserted, a short rod having the same diameter as the rod, with the short rod being directed in a direction substantially orthogonal to an axial direction of the through-hole and having a length required f or the short rod to be inserted and screwed into the through-hole, and an internal thread portion that allows an external thread member to be screwed therein, with the external thread member locking the rod or short rod inserted into the through-hole; and in which configuration a first connector can be set on the rod by inserting the rod into the through-hole therein, the short rod of a second connector can be arranged in a rod-attaching portion of a bone screw, and the short rod of the first connector can be inserted into the through-hole in the second connector.

4 Claims, 5 Drawing Sheets

SPINAL-ROD CONNECTING APPARATUS AND A CONNECTOR THEREOF

FIELD OF THE INVENTION

The present invention relates to a spinal-rod connecting apparatus for connecting and supporting bone screws implanted in vertebrae and rods installed in parallel to the vertebrae.

DESCRIPTION OF THE PRIOR ART

An operation is performed that holds the spine in a desirable position by implanting a required number of bone screws in vertebrae and connecting them to rods. Each of the bone screws has a connecting portion through which the rod is inserted and screwed. Such connecting portions are roughly divided into those shaped like holes formed in what are referred to as "closed screws," into which rods are inserted in an axial direction, and those shaped like grooves formed in what are referred to as "open screws" for receiving rods therein. However, it may be impossible or difficult to place a rod directly at the corresponding bone screw, that is, at the screw-connecting portion, depending on the site at which the rod is attached. In such cases, it is contemplated that an auxiliary part having a rod may be used. However, in accordance with the object of the auxiliary part, the physician must bend or cut this part in the operating room prior to operation. This is impractical.

SUMMARY OF THE INVENTION

The present invention is provided in view of the above points, and it is an object thereof to avoid requiring the physicians to machine, during operation, a connecting apparatus in the operating room, and to allow them to fix rods and bone screws together easily and accurately through the appropriate combination of connectors. It is another object of the present invention to provide a connector that can be preferably used for a spinal-rod connecting apparatus.

These and other objects are attained by a spinal-rod connecting apparatus of the present invention using multiple connectors, each comprising a through-hole through which a rod can be inserted, a short rod having the same diameter as the above rod, with the short rod being directed in a direction substantially orthogonal to an axial direction of the through-hole, and having a length required for the short rod to be inserted and screwed into the through-hole, and an internal thread portion that allows an external thread member to be screwed therein, with the external thread member locking the rod or short rod inserted into the through-hole, wherein a first connector can be set on the rod by inserting the rod into the through-hole therein, the short rod of a second connector can be arranged in a rod-attaching portion of a bone screw, and the short rod of the first connector can be inserted into the through-hole in the second connector.

The spinal-rod connecting apparatus according to the present invention uses connectors each comprising a through-hole through which a rod can be inserted, a short rod having the same diameter as the above rod, with the short rod being directed in a direction substantially orthogonal to an axial direction of the through-hole and having a length required for the short rod to be inserted and screwed into the through-hole, and an internal thread portion that allows an external thread member to be screwed therein, with the external thread member locking the rod or short rod inserted into the through-hole. In addition to the rod and short rod, a transverse rod that links parallel rods together can be inserted into the through-hole. The spinal-rod connecting apparatus according to the present invention connects and supports bone screws implanted in vertebrae, and rods installed in parallel to the vertebrae. The bone screw includes a screw or is a part called an "implant" having a connecting portion into which the rod is inserted and screwed. It does not matter whether the connection portion is of a closed type (hole) or an open type (groove).

The spinal-rod connecting apparatus according to the present invention uses multiple connectors. The connector desirably comprises a through-hole through which a rod can be inserted, a short rod having the same diameter as the above rod, with the short rod being directed in a direction substantially orthogonal to an axial direction of the through-hole, and an internal thread portion that allows an external thread member to be screwed therein, with the external thread member locking the rod or short rod inserted into the through-hole. That is, the short rod and the rod are adapted so as to be freely inserted and screwed into the through-hole in the connector. The short rod is of a length required for it to be inserted and screwed into a through-hole in another connector. Thus, the short rod need not be as long as the long rods found in conventional auxiliary parts.

The through-hole and short rod provided in the connector have an orthogonal relationship, as this arrangement allows the connector to be easily positioned orthogonal to or in parallel to the vertebrae. Further, the spinal-rod connecting apparatus consists of at least two connectors. These connectors may be of the same shape, minimizing the time and costs required for manufacturing the apparatus.

With the multiple connectors, a first connector is set on a rod by inserting the rod into the through-hole therein, the short rod of a second connector is arranged in a rod-attaching portion of a bone screw, and the short rod of the first connector is inserted into the through-hole in the second connector. When the multiple connectors are thus combined, the inclination or the like of the connectors can be corrected by aligning them with the bone screws implanted in the vertebrae, while keeping them parallel with the rods installed in parallel to the vertebrae. That is, the present invention has the advantage of being capable of three-dimensionally modifying the direction in which the bone screws are inserted into the rods when the rods and bone screws are connected.

BRIEF DESCRIPTION OF THE DRAWINGS

FIG. 8(*b*) is a side view showing an example of how the apparatus according to the present invention is adjusted.

DETAILED DESCRIPTION OF EMBODIMENTS

Figure 1:
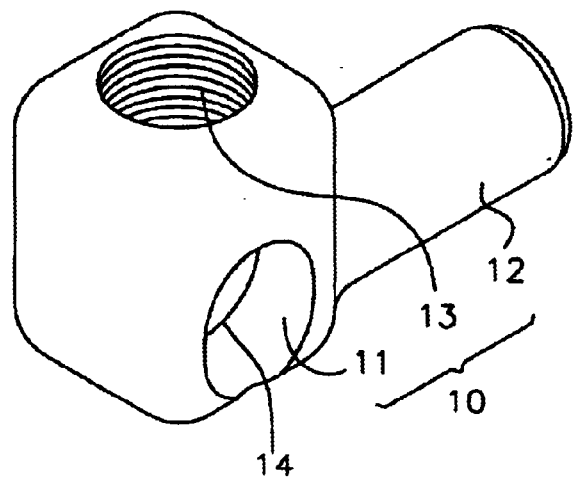
FIG. 1 is a perspective view showing Embodiment 1 of the connectors of a spinal-rod connecting apparatus according to the present invention.
Figure 2:
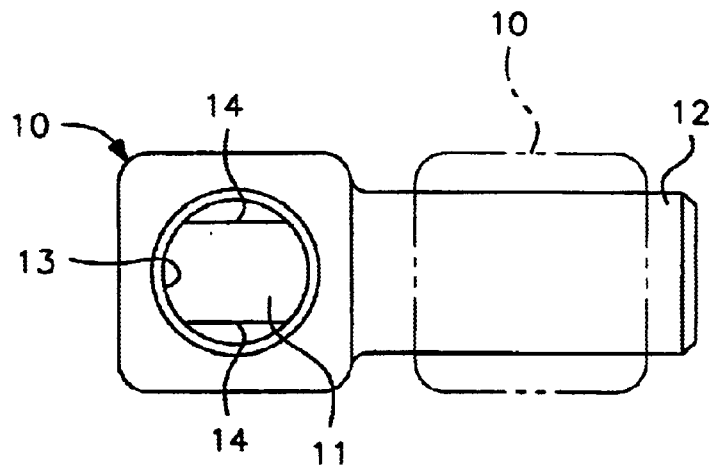
FIG. 2 is a top view showing the connectors shown in FIG. 1.
Figure 3:
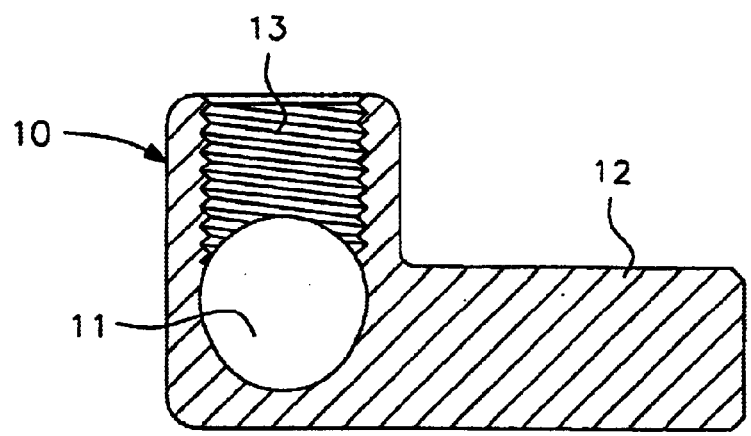
FIG. 3 is a longitudinal sectional view showing the connectors shown in FIG. 1.

The present invention will be described below in detail with reference to embodiments thereof. FIGS. 1 to 3 show Embodiment 1. This embodiment 1 shows an example of a connector 10. This connector has a through-hole 11 through which a rod 15 can be inserted, a short rod 12 extending orthogonally to the axis of the through-hole 11, and an internal thread portion 13 formed so as to reach the through-hole 11, and in which a screw locks the rod 15 or short rod 12 that is inserted into the through-hole 11.

The connector 10 of Embodiment 1 is an example in which the short rod 12 is provided at a lower position that can be as low as the position of the through-hole 11. The short rod 12 is of a length required to be screwed into the through-hole in another connector 10 (see FIG. 2), and is integrated with the portion having the through-hole 11. Due to its lower position, the through-hole 11 can be connected to a bone-screw member 30 installed in a vertebra 33. The through-hole 11 is designed to enlarge the opposite ends by inversely tapering them so that the rod can easily be inserted into the through-hole 11, and so that the acting force of the screwing is concentrated between corners 14, 14 bordering on the inversely tapered portions.

The internal thread portion 13 and thus an external thread member 25 screwed therein have a diameter set so as not to be significantly smaller than the diameter of the rod 15 (FIG. 3). Further, the through-hole 11 has a slightly smaller diameter than the radius of rod 15, and is formed so that the through-hole has a radius slightly greater than that of the round bottom, with the latter circle slightly displaced to the side from concentricity with the larger hole when viewed from the mouth side so that when tightened, the external thread member 25 is forcibly fitted into the through-hole (FIG. 3).

Figure 4:
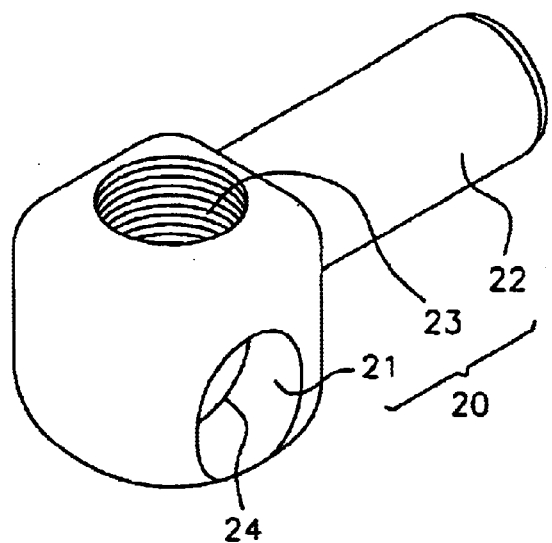
FIG. 4 is a perspective view showing Embodiment 2 of connectors according to the present invention.
Figure 5:
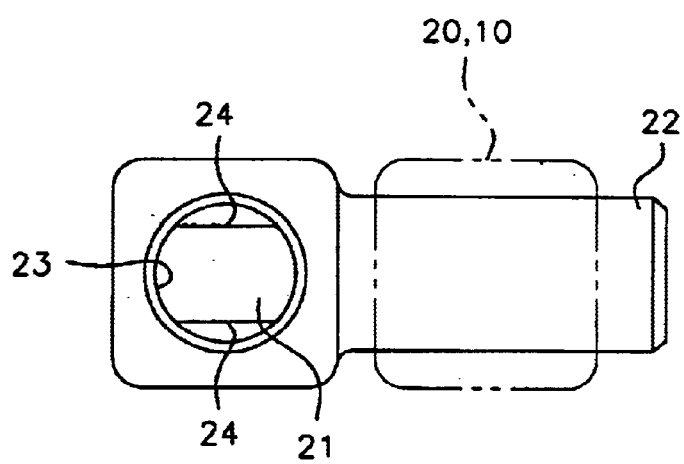
FIG. 5 is a top view of the connectors shown in FIG. 4.
Figure 6:
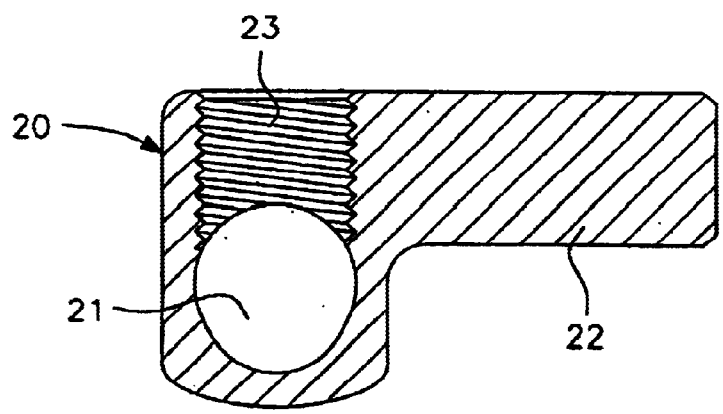
FIG. 6 is a longitudinal sectional view of the connectors shown in FIG. 4.

FIGS. 4 to 6 show a connector 20 according to Embodiment 2. The connector 20 in Embodiment 2 has a short rod 22 located higher than the through-hole 21. The length of the short rod 22, an internal thread portion 23 formed so as to reach the through-hole 21, and the like are the same as those in Embodiment 1. Further, the through-hole 21 also has an inversely tapered portion so as to concentrate the acting force of the screwing between the corners 24, 24.

In Embodiment 2, since the through-hole 21 is formed at a lower position, the rod 15 can be arranged at a relatively lower position. The internal thread portion 23 is formed over such a length that the external thread member 25 can be screwed with sufficient force into the internal thread portion 23. When the external thread member 25 is tightened, its head is entirely accommodated within the connector 20 or hardly projects therefrom. This also applies to Embodiment 1.

Figure 7:
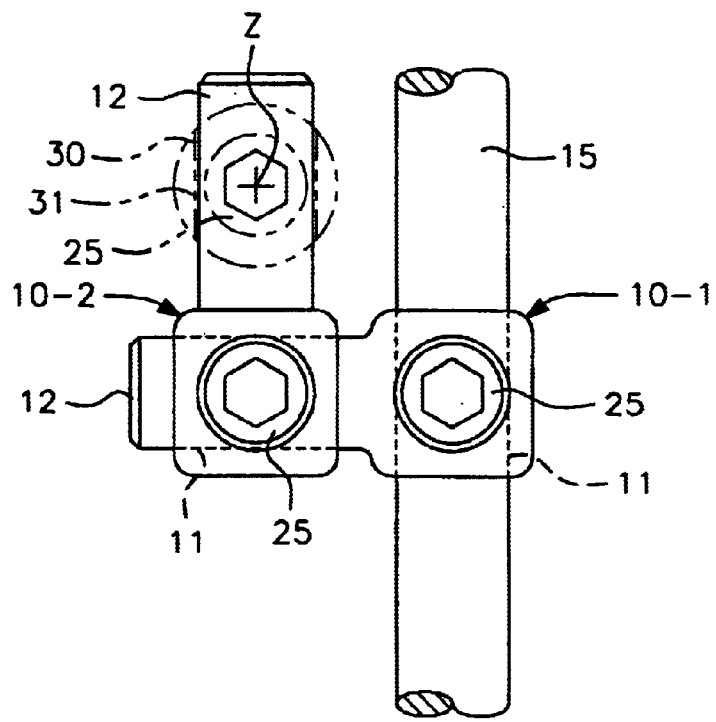
FIG. 7 is a top view showing an example of an arrangement of the apparatus according to the present invention.

The connector 10 in Embodiment 1 and the connector 20 in Embodiment 2 may be used together or separately. In operation, for example, as shown in FIG. 7, a first connector 10-1 is set on the rod 15 by inserting the rod 15 into the through-hole 11 therein, the short rod 12 of a second connector 10-2 is arranged in a rod-attaching portion 31 of a bone screw member 30, and the short rod 12 of the first connector 10-1 is inserted into the through-hole 11 in the second connector 10-2. The first connector 10-1 is fixed to the rod 15 by insertion, and the second connector 10-2 is fixed to the bone screw member 30; these do not refer to the connectors of Embodiments 1 and 2.

Figure 8A:
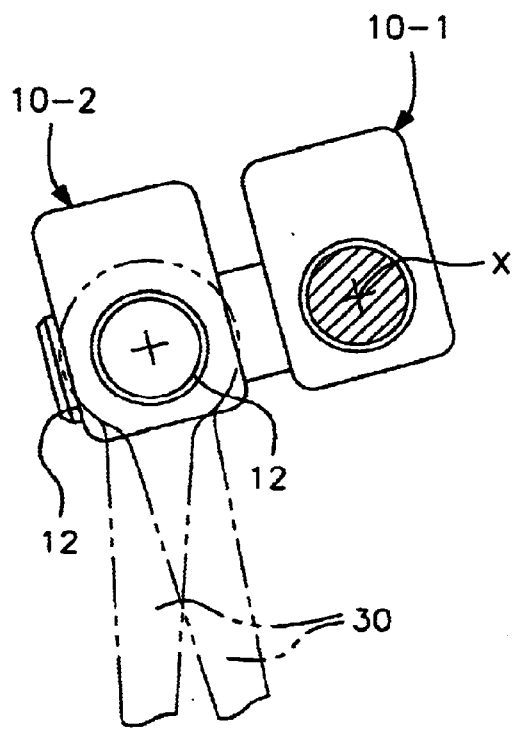
FIG. 8(*a*) is a transversal sectional view showing an example of how the apparatus according to the present invention is adjusted.
Figure 8B:
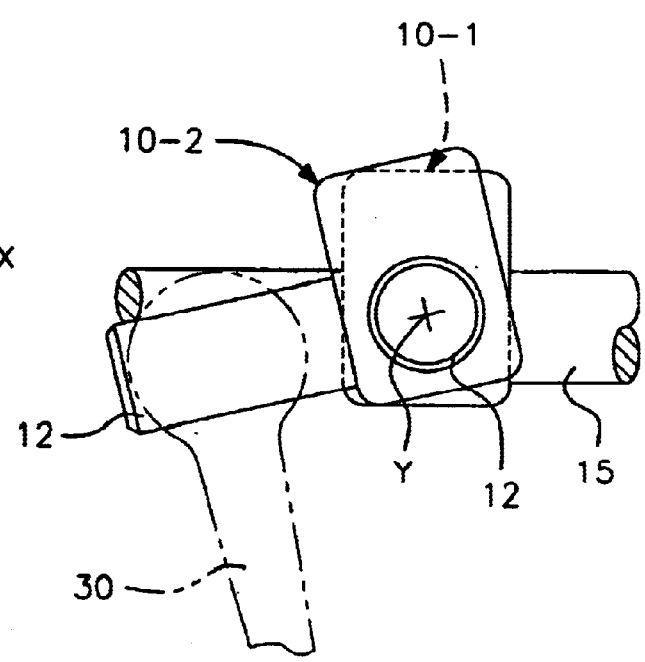
Figure 9:
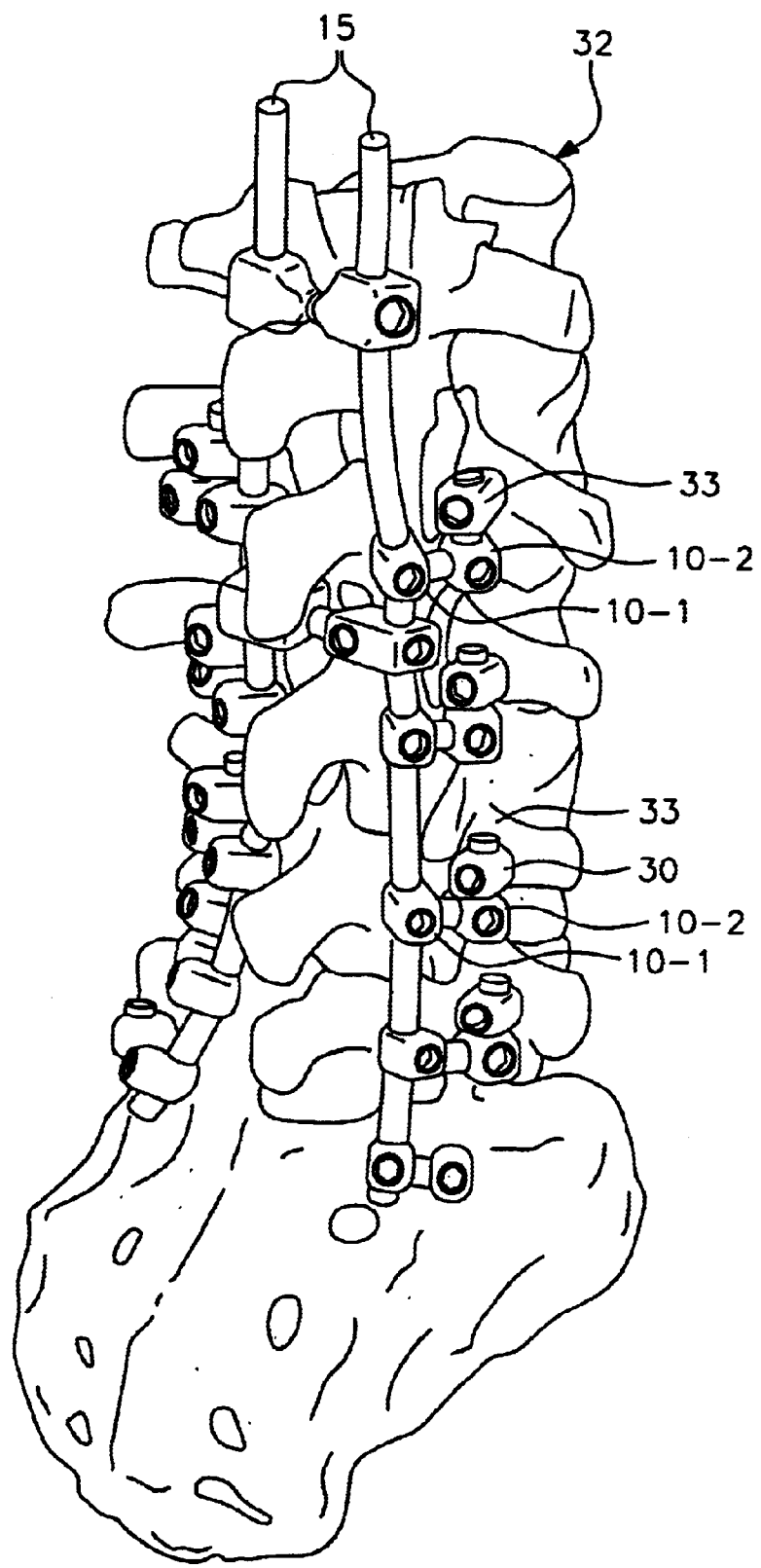
FIG. 9 is a perspective view of an example in which the present apparatus is applied to a spinal correction.
Figure 10A:
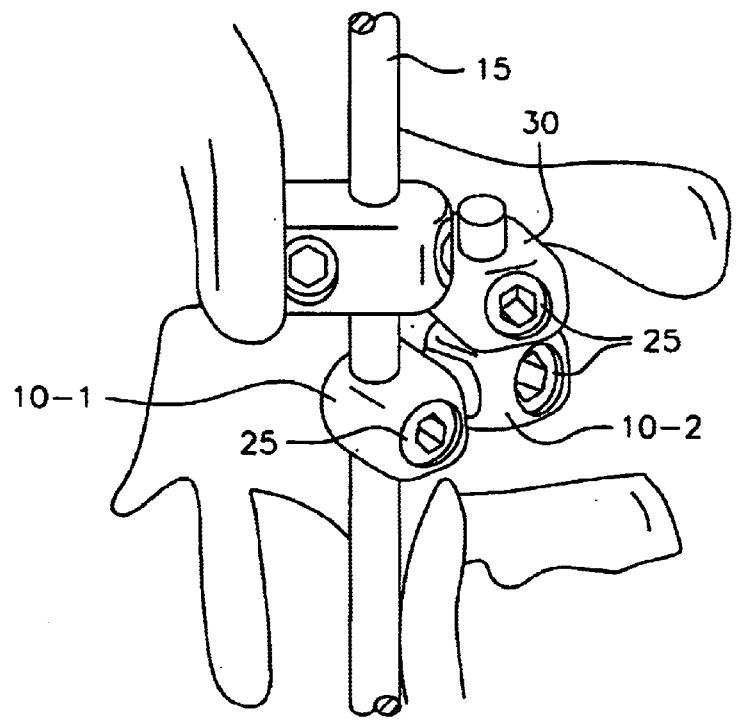
FIG. 10(a) is a partially enlarged view of FIG. 9.
Figure 10B:
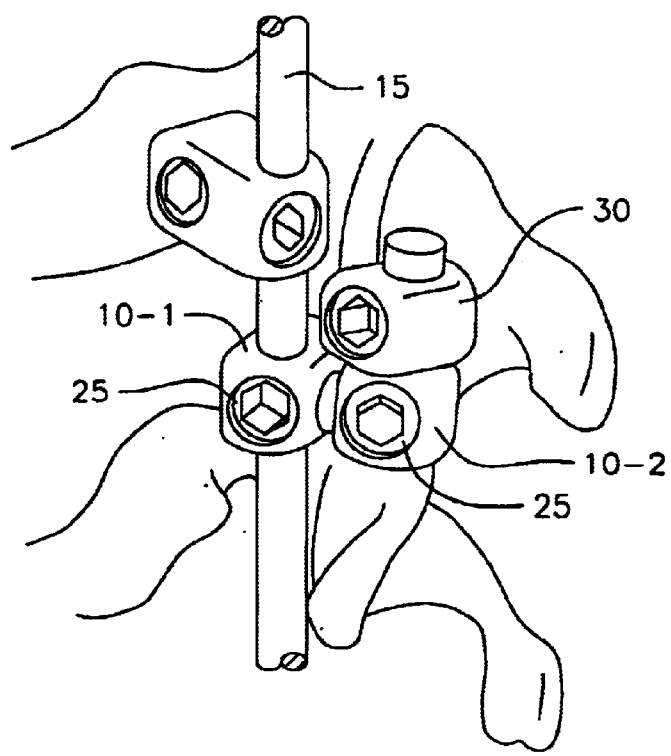
FIG. 10(b) is an enlarged view similar to FIG. 10(a), but seen from a different angle.

FIG. 7 shows an example in which the bone screw member 30 can be directed to directions of three axes X, Y, and Z which are orthogonal to each other; the bone screw member 30 is fitted, by insertion, on the short rod 12 of the second connector 10-2, which is fitted, by insertion, on the short rods 12 of the first connectors 10-1, which is inserted into the rods 15. The first connector 10-1 can be rotated for adjustments relative to the X-axis, and the second connector 10-2 can be rotated for adjustments relative to the Y-axis. The short rod 12 of the first connector 10-1 enables adjustments relative to the Y-axis (FIG. 8(b)), and the short rod 12 of the second connector 10-2 enables rotation of the bone screw member 30 (FIG. 8(a)). FIG. 9 shows an example of an apparatus that connects and supports bone-screw members 30 implanted in the vertebrae 33 constituting the spine 32, and rods 15 arranged in parallel to the vertebrae 33. An essential part of FIG. 9 is enlarged and shown from various perspectives in FIGS. 10(a) and 10(b). As is apparent from these figures, although the bone-screw members 30 are screwed into the vertebrae 33 in slightly different positions, the apparatus of the present invention absorbs differences between the positions of the bone-screw members and the direction of the rods 15, thereby enabling accurate and fixed positioning.

Since the present invention is constituted and operated as described above, bone-screw members implanted in the vertebrae by combining multiple connectors and rods installed in parallel to the vertebrae can be linked and, connected, and supported together by screwing. Consequently, during an operation, it is not necessary for the physician to machine a connecting apparatus for adjustments in the operating room; auxiliary parts machined in a conventional manner can be handled by appropriately combining the connectors. Therefore, the physician can easily and accurately fix the rods and bone-screw members together.

What is claimed is:

1. A spinal-rod connecting apparatus for connecting and supporting bone screws implanted in vertebrae and rods installed in parallel to the vertebrae, the apparatus comprising multiple connectors, each connector comprising an elongated body having two opposing ends with a through-hole located at one of the two opposing ends through which an elongated rod can be inserted, a short rod extending from either of the two opposing ends of the elongated body and the short rod having a same diameter as said elongated rod, with the short rod being directed in a direction substantially orthogonal to an axial direction of the through-hole and having a length required for the short rod to be inserted and retained in the through-hole, and an internal thread portion of the elongated body, an external thread member to be screwed in the internal thread portion, with the external thread member locking the elongated rod or short rod inserted into the through-hole, wherein a first connector of the multiple connectors can be set on the elongated rod by inserting the elongated rod into the through-hole therein, the short rod of a second connector of the multiple connectors can be arranged in a rod-attaching portion of a bone screw, and the short rod of the first connector can be inserted into the through-hole in the second connector so as to allow connecting of the bone screw and the short rod without bending the elongated rod.

2. The spinal-rod supporting apparatus according to claim 1, wherein a short rod is provided at a lower position at the one end of the two opposing ends of the elongated body that can be as low as a position of the through-hole.

3. The spinal-rod supporting apparatus according to claim 1, wherein a short rod is provided at a higher position than the through-hole at the other end of the two opposing ends of the elongated body.

4. A connector for use in a spinal-rod connecting apparatus for connecting and supporting bone screws implanted in vertebrae and rods installed in parallel to the vertebrae, the connector comprising an elongated body having a two opposing ends with a through-hole located at one of the two opposing ends through which an elongated rod can be inserted, a short rod extending from either of the two opposing ends of the elongated body and the short rod having a same diameter as said elongated rod, with the short rod being directed in a direction substantially orthogonal to an axial direction of the through-hole and having a length required for the short rod to b be inserted and retained in the through-hole, and an internal thread portion of the elongated body, an external thread member to be screwed in the internal thread portion, with the external thread member locking the elongated rod or short rod inserted into the through-hole.

\* \* \* \* \*